US008501696B2

(12) United States Patent
Grötzinger et al.

(10) Patent No.: US 8,501,696 B2
(45) Date of Patent: Aug. 6, 2013

(54) SOLUBLE GP130 MUTEINS WITH IMPROVED BINDING ACTIVITY

(75) Inventors: Joachim Grötzinger, Altwittenbek (DE); Jürgen Scheller, Kiel (DE); Stephanie Tenhumberg, Schwetzingen (DE); Stefan Rose-John, Schellhorn (DE); Georg H. Wätzig, Kiel (DE)

(73) Assignee: Conaris Research Institute AG, Kiel (DE)

( * ) Notice: Subject to any disclaimer, the term of this patent is extended or adjusted under 35 U.S.C. 154(b) by 184 days.

(21) Appl. No.: 12/738,807

(22) PCT Filed: Oct. 15, 2008

(86) PCT No.: PCT/EP2008/008736
§ 371 (c)(1),
(2), (4) Date: Aug. 16, 2010

(87) PCT Pub. No.: WO2009/049881
PCT Pub. Date: Apr. 23, 2009

(65) Prior Publication Data
US 2010/0298236 A1      Nov. 25, 2010

(30) Foreign Application Priority Data

Oct. 19, 2007  (EP) .................................... 07020512
May 27, 2008  (EP) .................................... 08009648

(51) Int. Cl.
*A61K 38/17*    (2006.01)
*C07K 14/715*   (2006.01)

(52) U.S. Cl.
USPC ........................... 514/21.2; 530/350; 530/351

(58) Field of Classification Search
None
See application file for complete search history.

(56) References Cited

U.S. PATENT DOCUMENTS

| 6,605,703 | B1 | 8/2003 | Schaeffer et al. | |
| 7,534,862 | B2 * | 5/2009 | Seegert et al. | 530/350 |
| 7,629,147 | B2 * | 12/2009 | Seegert et al. | 435/69.1 |

FOREIGN PATENT DOCUMENTS

| DE | 199 41 897 | | 3/2001 |
| EP | 1 491 554 | | 12/2004 |
| EP | 1 801 121 | | 6/2007 |
| WO | WO 2008/000516 | * | 1/2008 |

OTHER PUBLICATIONS

Tenhumberg et al. "152 Characterization of Mutants of the Soluble CP130 Protein in Terms of their binding affinity against the IL6/SIL6R Complex." *Cytokine Abstracts*. vol. 39. 2007. pp. 42.
Bitter et al. "Expression and Secretion Vectors for Yeast." *Methods in Enzymology*. vol. 153. 1987. pp. 516-545.
Boulanger et al. "Hexameric Structure and Assembly of the Interleukin-6/IL-6 α-Recptor/gp 130 Complex." *Science*. vol. 300. 2003. pp. 2101-2104.
Boulanger et al. "Materials & Methods." 2003. 5 pages.
Broglie et al. "Light-Regulated Expression of a Pea Ribulose-1, 5-Bisphosphate Carboxylase Small Subunit Gene in Transformed Plant Cells." *Science*. vol. 224. 1984. pp. 838-843.
Chalaris et al. "Apoptosis is a natural stimulus of IL6R shedding and contributeds to the proinflammatory trans-signaling function of neutrophils." *Blood*. vol. 110. No. 6. 2007. pp. 1748-1755.
Colbere-Garapin et al. "A New Dominant Hybrid Selective Marker for Higher Eukaryotic Cells." *J. Mol. Biol.* vol. 150. 1981. pp. 1-14.
Coruzzi et al. "Tissue-specific and light-regulated expression of a pea nuclear gene encoding the small subunit of ribulos-1, 5-bisphosphate carboxylase." *The EMBO J*. vol. 3. No. 8. 1984. pp. 1671-1679.
Darnell, Jr. et al. "STATs and Gene Regulation." *Science* vol. 277. 1997. pp. 1630-1635.
Edwards et al. "The Formation of a structure with the features of synovial lining by subcutaneous injection of air: an in vivo tissue culture system." *J. Pathology*. vol. 134. 1981. pp. 147-156.
Engelhard et al. "The insect tracheal system: A conduit for the systemic spread of *Autographa californica* M nuclear polyhedrosis virus." *Proc. Natl. Acad. Sci.* vol. 91. 1994. pp. 3224-3227.
Fingl et al. "The Pharmacological Basis of Therapeutics. Pharmacokinetics." *Goodman and Gilman eds. Macmillan Publishing Co. NY.* 1975 pp. 1-46.
Fischer et al. "A bioactive designer cytokine for human hematopoietic progenitor cell expansion." *Nature Biotechnology*. vol. 15. 1997. pp. 142-145.
Gellissen et al. "New yeast expression platforms based on methylotrophic *Hansenula polymorpha* and *Pichia pastoris* and on dimorphic *Arxula adeninivorans* and *Yarrowia lipolytica* —a comparison." *FEMS Yeast Research*. vol. 5. 2005. pp. 1079-1096.
Gomord et al. "Biopharmaceutical production in plants: problems, solutions and opportunities." *Trends in Biotechnology*. vol. 23. No. 11. 2005. pp. 559-565.
Goodson et al. "Site-Directed Pegylation of Recombinant interleukin-2 at it sglycosylation site." *Biotech*. vol. 8. 1990. pp. 343-346.
Grace et al. "Structural and Biologic Characterization of Peglated Recombinant IFN-α2b." *J. of Interferon and Cytokine Research*. vol. 21. 2001. pp. 1103-1115.
Grotzinger et al. "IL-6Type Cytokine Receptor Complexes: Hexamer, Tetramer or Both?" *Biol. Chem*. vol. 380. 1999. pp. 803-813.
Grotzinger et al. "The Family of the IL-6-Type Cytokines: Specificity and Promiscuity of the Receptor Complexes." *Proteins: Structure, Function and Genetics*. vol. 27. 1997. pp. 96-109.

(Continued)

*Primary Examiner* — Marianne P Allen
(74) *Attorney, Agent, or Firm* — Choate, Hall & Stewart LLP; Brenda H. Jarrell; Rolando Medina

(57) ABSTRACT

Described are soluble gp130 polypeptide monomers and dimers, wherein, in a preferred embodiment, at least one of the three amino acid residues $Thr_{102}$ $Gln_{113}$ or $Asn_{114}$ of the N-terminal Ig-like domain of gp130 is mutated to $Tyr_{102}$, $Phe_{113}$ or $Leu_{114}$, respectively. These mutations, alone or in combination, specifically enhance binding of gp130 to its ligand complex of interleukin-6 and soluble interleukin-6 receptor, thus increasing the biological activity of the gp130 muteins. In a particularly preferred embodiment, all three mutations are combined in the triple mutein Thr102Tyr/Gln113Phe/Asn114Leu (T102Y/Q113F/N114L). Moreover, a pharmaceutical composition containing said monomers or dimers and various medical uses are described.

24 Claims, 8 Drawing Sheets

OTHER PUBLICATIONS

Hartman et al. "Two dominant-acting selectable markers for gene transfer studies in mammalian cells." *Proc. Natl. Acad. Sci.* vol. 85. 1988. pp. 8047-8051.

Katre. "Immunogenicity of Recombinant IL-2 Modified by Covalent attachment of polyethylene glycol." *J. of Immunology.* vol. 144. No. 1. 1990. pp. 209-213.

Kishimoto et al. "Interleukin-6 Family of Cytokines and gp130." *Blood.* vol. 86. No. 4. 1995. pp. 1243-1254.

Kohler et al. "Continuous cultures of fused cells secreting antibody of predefined specificity." *Nature.* vol. 256. 1975. pp. 495-497.

Logan et al. "Adenovirus tripartite leader sequence enhances translation of mRNAs late after infection." *Proc. Natl. Acad. Sci.* vol. 81. 1984. pp. 3655-3659.

Lowy et al. "Isolation of Transforming DNA: Cloning the Hamster aprt Gene." *Cell.* vol. 22. 1980. pp. 817-823.

Macauley-Patrick et al. "Heterologous protein production using the *Pichia pastoris* expression system." *Yeast.* vol. 22. 2005. pp. 249-270.

Murry. "Genetic engineering." *McGraw Hill Yearbook of Science and Technology.* 1992. pp. 191-196.

Oppmann et al. "Alternative assay procedures for cytokines and soluble receptors of the IL-6 family." *J. of Immunological Methods.* vol. 195. 1996. pp. 153-159.

Pepinsky et al. "Improved Pharmacokinetic Properties of a Polyethylene Glycol-Modified Form of the Interferon-β-1a with Preserved in Vitro bioactivity." *J. of Pharm. and Exp. Thera.* vol. 297. No. 3. 2001. pp. 1059-1066.

Peters et al. "In vivo and in vivo activities of the gp130-Stimulating Desinger Cytokine Hyper-IL-6." *J. of Immunology.* vol. 161. 1998. pp. 3575-3581.

Petit et al. "Structure-Function Studies of Interleukin 15 using Site-specific Mutagenesis, Polyethylene Glycol Conjugation, and Homology Modeling." *J. of Biological Chem.* vol. 272. No. 4. 1997. pp. 2312-2318.

Rose-John et al. "Studies on the structure and regulation of the human hepatic interleukin-6 receptor." *Eur. J. Biochem.* vol. 190. 1990. pp. 79-83.

Siam et al. "Choosing and using *Schizosaccharomyces pombe* plasmids." *Methods.* vol. 33. 2004. pp. 189-198.

Sprang et al. "Cytokine structural taxonomy and mechanisms of receptor engagement." *Current Opinion in Structural Biology.* vol. 3. 1993. pp. 815-8227.

Stoger et al. "Sowing the seeds of success: pharmaceutical proteins from plants." *Current Opinion in Biotechnology.* vol. 16. 2005. pp. 167-173.

Takamatsu et al. "Expression of bacterial chloramphenicol acetyltransferase gene in tobacco plants mediated by TMV-RNA." *The EMBO J.* vol. 6. No. 2. 1987. pp. 307-311.

Vriend. "What if: A molecular modeling and drug design program." *J. Mol. Graphics.* vol. 8. 1990. pp. 52-56.

Waetzig et al. "p38 Mitogen-Activated Protein Kinase Is activated and linked to TNF-α Signaling in Inflammatory Bowel Disease." *J. of Immunology.* vol. 168. 2002. pp. 5342-5351.

Wahl et al. "Improved Radioimaging and Tumor Localization with Monoclonal F(ab')$_2$." *J. of Nuclear Medicine.* vol. 24. 1983. pp. 316-325.

Wigler et al. "Transfer of Purified Herpes Virus Thymidine Kinase Gene to Cultured Mouse cells." *Cell.* vol. 11. 1977. pp. 223-232.

Wigler et al. "Transformation of mammalian cells with an amplifiable dominant-acting gene." *Proc. Natl. Acad. Sci.* vol. 77. No. 6. 1980. pp. 3567-3570.

Wildt et al. "The Humanization of N-Glycosylation Pathways in Yeast." *Nature Reviews.* vol. 3. 2005. pp. 119-128.

Winter et al. "The Expression of Heat Shock Protein and Cognate Genes During Plant Development." *Results and Problems in Cell Differentiation.* vol. 17. 1991. pp. 85-105.

Youngster et al. "Structure, Biology, and Therapeutic Implications of Pegylated Interferon Alpha-2b." *Current Pharmaceutical Design.* vol. 8. 2002. pp. 2139-2157.

* cited by examiner

Fig. 1

N-terminal domain of gp130

*MLTLQTWLVQALFIFLTTEST*GELLDPCGYISPESPVVQLHSNFTA
VCVLKEKCMDYFHVNANYIVWKTNHFTIPKEQYTIINRTASSVTFT
DIASLNIQL<u>T</u>CNILTFGQLE<u>QN</u>VYG... SEQ ID NO:2

*italic*     = signal peptide
<u>underlined</u> = immunoglobulin-like (Ig) domain
T, Q, N = $Thr_{102}$ (T), $Gln_{113}$ (Q) and $Asn_{114}$ (N)

Sequence alignment of wildtype and muteins

...IQLTCNILTFGQLEQNVYG... wildtype (SEQ ID NO:3)

...IQL1CNILTFGQLE2 3VYG... mutation scheme

...IQLYCNILTFGQLEQNVYG... T102Y ($Thr_{102}$ → $Tyr_{102}$) (SEQ ID NO:4)
...IQLTCNILTFGQLEFNVYG... Q113F ($Gln_{113}$ → $Phe_{113}$) (SEQ ID NO:5)
...IQLTCNILTFGQLEQLVYG... N114L ($Asn_{114}$ → $Leu_{114}$) (SEQ ID NO:6)

...IQLYCNILTFGQLEFNVYG... T102Y/Q113F (SEQ ID NO:7)
...IQLYCNILTFGQLEQLVYG... T102Y/N114L (SEQ ID NO:8)
...IQLTCNILTFGQLEFLVYG... Q113F/N114L (SEQ ID NO:9)
...IQLYCNILTFGQLEFLVYG... T102Y/Q113F/N114L (SEQ ID NO:10)

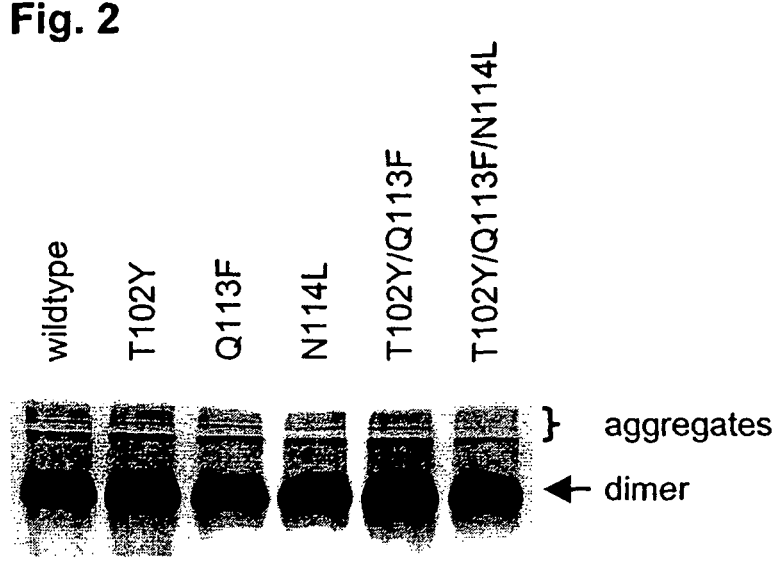

Haptoglobin secretion from HepG2 cells measured by ELISA

Fig. 5

|  | $k_{on}$ [1/Ms] | $k_{off}$ [1/s] | $K_D$ [M] |
|---|---|---|---|
| wild type sgp130Fc | $5.00 \times 10^5 \pm 893.9$ | $2.50 \times 10^{-4} \pm 2.00 \times 10^{-6}$ | $4.99 \times 10^{-10}$ |
| T102Y/Q113F/N114L | $5.42 \times 10^5 \pm 620.8$ | $6.63 \times 10^{-5} \pm 1.33 \times 10^{-6}$ | $1.22 \times 10^{-10}$ |

SEQUENCE LISTING

```
<160> NUMBER OF SEQ ID NOS: 10

<210> SEQ ID NO 1
<211> LENGTH: 6
<212> TYPE: PRT
<213> ORGANISM: artificial sequence
<220> FEATURE:
<223> OTHER INFORMATION: glycosylation linker

<400> SEQUENCE: 1

His Asn Leu Ser Val Ile
1               5

<210> SEQ ID NO 2
<211> LENGTH: 117
<212> TYPE: PRT
<213> ORGANISM: Homo sapiens

<400> SEQUENCE: 2

Met Leu Thr Leu Gln Thr Trp Leu Val Gln Ala Leu Phe Ile Phe Leu
1               5                   10                  15

Thr Thr Glu Ser Thr Gly Glu Leu Leu Asp Pro Cys Gly Tyr Ile Ser
            20                  25                  30

Pro Glu Ser Pro Val Val Gln Leu His Ser Asn Phe Thr Ala Val Cys
        35                  40                  45

Val Leu Lys Glu Lys Cys Met Asp Tyr Phe His Val Asn Ala Asn Tyr
    50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
            100                 105                 110

Gln Asn Val Tyr Gly
        115

<210> SEQ ID NO 3
<211> LENGTH: 19
<212> TYPE: PRT
<213> ORGANISM: Homo sapiens

<400> SEQUENCE: 3

Ile Gln Leu Thr Cys Asn Ile Leu Thr Phe Gly Gln Leu Glu Gln Asn
1               5                   10                  15

Val Tyr Gly

<210> SEQ ID NO 4
<211> LENGTH: 19
<212> TYPE: PRT
<213> ORGANISM: artificial sequence
<220> FEATURE:
<223> OTHER INFORMATION: T102Y mutein
```

```
<400> SEQUENCE: 4

Ile Gln Leu Tyr Cys Asn Ile Leu Thr Phe Gly Gln Leu Glu Gln Asn
1               5                   10                  15

Val Tyr Gly

<210> SEQ ID NO 5
<211> LENGTH: 19
<212> TYPE: PRT
<213> ORGANISM: artificial sequence
<220> FEATURE:
<223> OTHER INFORMATION: Q113F mutein

<400> SEQUENCE: 5

Ile Gln Leu Thr Cys Asn Ile Leu Thr Phe Gly Gln Leu Glu Phe Asn
1               5                   10                  15

Val Tyr Gly

<210> SEQ ID NO 6
<211> LENGTH: 19
<212> TYPE: PRT
<213> ORGANISM: artificial sequence
<220> FEATURE:
<223> OTHER INFORMATION: N114L mutein

<400> SEQUENCE: 6

Ile Gln Leu Thr Cys Asn Ile Leu Thr Phe Gly Gln Leu Glu Gln Leu
1               5                   10                  15

Val Tyr Gly

<210> SEQ ID NO 7
<211> LENGTH: 19
<212> TYPE: PRT
<213> ORGANISM: artificial sequence
<220> FEATURE:
<223> OTHER INFORMATION: T102Y/Q113F mutein

<400> SEQUENCE: 7

Ile Gln Leu Tyr Cys Asn Ile Leu Thr Phe Gly Gln Leu Glu Phe Asn
1               5                   10                  15

Val Tyr Gly

<210> SEQ ID NO 8
<211> LENGTH: 19
<212> TYPE: PRT
<213> ORGANISM: artificial sequence
<220> FEATURE:
<223> OTHER INFORMATION: T102Y/N114L mutein

<400> SEQUENCE: 8

Ile Gln Leu Tyr Cys Asn Ile Leu Thr Phe Gly Gln Leu Glu Gln Leu
1               5                   10                  15

Val Tyr Gly

<210> SEQ ID NO 9
<211> LENGTH: 19
<212> TYPE: PRT
<213> ORGANISM: artificial sequence
<220> FEATURE:
<223> OTHER INFORMATION: Q113F/N114L mutein

<400> SEQUENCE: 9

Ile Gln Leu Thr Cys Asn Ile Leu Thr Phe Gly Gln Leu Glu Phe Leu
1               5                   10                  15
```

```
Val Tyr Gly

<210> SEQ ID NO 10
<211> LENGTH: 19
<212> TYPE: PRT
<213> ORGANISM: artificial sequence
<220> FEATURE:
<223> OTHER INFORMATION: T102Y/Q113F/N114L mutein

<400> SEQUENCE: 10

Ile Gln Leu Tyr Cys Asn Ile Leu Thr Phe Gly Gln Leu Glu Phe Leu
1               5                   10                  15

Val Tyr Gly
```

SOLUBLE GP130 MUTEINS WITH IMPROVED BINDING ACTIVITY

This application is a National Stage Application of PCT/EP2008/008736, filed 15 Oct. 2008, which claims benefit of Serial No. 07 020 512.5, filed 19 Oct. 2007 in Europe and Serial No. 08 009 648.0, filed 27 May 2008 in Europe and which applications are incorporated herein by reference. To the extent appropriate, a claim of priority is made to each of the above disclosed applications.

The present invention relates to muteins of glycoprotein gp130 polypeptides with improved binding activity for the ligand complex consisting of interleukin-6 (IL-6) and its soluble receptor (sIL-6R). In particular, a polypeptide dimer comprising two identical muteins of the gp130 extracellular domain (soluble gp130, sgp130) each being fused to an Fc domain of an IgG protein (sgp130Fc) shows improved bioactivity. The present invention also relates to a pharmaceutical composition containing mutated sgp130 polypeptides (sgp130 muteins) or dimers thereof and various medical uses.

The pleiotropic cytokine interleukin-6 (IL-6) shows a wide spectrum of biological functions among which stimulation of B cells and induction of acute phase protein synthesis in liver are mostly notable. IL-6 belongs to the family of four-helix-bundle cytokines. The structure of the cytokine consists of four helices (A, B, C and D) connected by one long loop (AB), one short loop (BC) and again one long loop (CD). IL-6 signals via a complex of IL-6, IL-6 receptor (IL-6R) and two gp130 molecules on the cell surface (Kishimoto et al. (1995) Blood 86:1243-54). The ligand-induced activation of the complex leads to the activation of associated Janus kinases (JAKs) which phosphorylate themselves and the cytoplasmic portion of gp130 (Darnell (1997) Science 277:1630-5). Soluble forms of the IL-6R (sIL-6R), which are generated by either alternative splicing or shedding are also able to trigger gp130 dimerization and signalling when complexed with IL-6.

Since the cytoplasmic portion of the IL-6R does not contribute to signal transduction, signalling by a gp130 homodimer can be induced by IL-6 in complex with membrane bound or soluble IL-6R. The presence of sIL-6R, however, leads to sensitization of IL-6-responsive cells towards the ligand. Furthermore, strictly IL-6-dependent hybridoma cells do not proliferate in response to very low amounts of IL-6 when sIL-6R present in culture media is continuously removed.

Beside IL-6, gp130 is also used by other members of the four-helix-bundle cytokine family such as IL-11, leukaemia inhibitory factor (LIF), cardiotropin-like cytokine (CLC), oncostatin M (OSM), ciliary neurotrophic factor (CNTF), cardiotropin-1 (CT-1) and neuropoietin (NPN) or the recently described cytokine IL-27. All of these cytokines act via a bi- or tripartite receptor complex in which signalling is triggered by homodimerization (for IL-6 and IL-11) or heterodimerization of gp130, e.g. with LIF-R (for LIF, CT-1, OSM, CLC and CNTF). These cytokines can thus mediate similar biological activities in various tissues.

While gp130 can be found on nearly all cell types, the IL-6R shows a much more restricted expression. The release of sIL-6R by one cell type renders other cells, which only express gp130, responsive to IL-6. This process is called trans-signalling. Indeed, several cellular activities have been described which require the complex of sIL-6R and IL-6 and are not observed with IL-6 alone. In the designer-cytokine Hyper-IL-6 (H-IL-6), the C-terminus of sIL-6R is covalently fused to the N-terminus of mature IL-6 by a flexible peptide linker (Fischer et al. (1997) Nat. Biotechnol. 15:142-5). As seen with the complex of IL-6/sIL-6R, H-IL-6 also acts on cells which only express gp130. In contrast to the separate components IL-6 and sIL-6R, a 100- to 1000-fold lower concentration of this fusion molecule is sufficient to induce comparable biological signals. IL-11, the other cytokine signalling through a gp130 homodimer, shows no trans-signalling, as the IL-11 receptor does not occur in a soluble form. Soluble gp130 protein is constitutively found in high concentrations in human plasma and functions as a natural buffer and inhibitor of IL-6 trans-signalling.

For the treatment of various diseases or disorders, specific blocking of IL-6 responses dependent on soluble IL-6R might be desirable. Such diseases include bone resorption, hypercalcemia, cachexia, tumors or other types of cancer (e.g., colon cancer, multiple myeloma, lymphoma, leukaemia, Hodgkin's disease or Castleman's disease), autoimmune diseases (e.g., multiple sclerosis (MS), type 1 diabetes or lupus erythematosus), inflammatory or atopic diseases (e.g., Crohn's disease, ulcerative colitis, rheumatoid arthritis, juvenile rheumatoid arthritis, asthma, psoriasis, sarcoidosis, uveitis or allergic conjunctivitis), infections (e.g., by bacteria, viruses, fungi or other pathogens), sepsis, as well as endocrinologic disorders and metabolic or catabolic diseases (e.g., type 2 diabetes, obesity, hyperglycemia or hypercholesterinemia). It was found that, e.g., sgp130 dimers or sgp130Fc dimers are useful for therapeutic applications designed to inhibit the actions of the agonistic IL-6/sIL-6R complex.

The regions of IL-6 which are in contact with the (soluble or membrane-bound) IL-6R and gp130 are called site I, II and III. IL-6R is bound to site I of IL-6. The co-receptor gp130 belongs to the class of tall cytokine receptors, which exhibit three fibronectin domains (D4-D6) between the ligand-binding domains and the transmembrane region of the receptors (Sprang and Bazan (1993) Curr. Opin. Struct. Biol. 3:815-27). The ligand binding domain of gp130 also consists of three domains (D1-D3): an N-terminal immunoglobulin (Ig)-like domain (D1) and two fibronectin type III-like domains (D2 and D3), of which the latter are called the cytokine binding module (Grötzinger et al. (1999) Biol. Chem. 380: 803-13). Whereas the N-terminal Ig-like domain of gp130 is in contact with site III of IL-6, the cytokine-binding module of gp130 binds to site II. The three-dimensional structure of the hexameric complex (IL-6/IL-6R/gp130)$_2$ has been solved (Boulanger et al. (2003) Science 300:2101-4). Interestingly, however, site III of IL-6 has not been resolved completely. The C-terminal part of helix A and the N-terminal part of the AB loop have not been resolved, although this region is part of the interaction site between IL-6 and gp130. So far, sgp130 variants showing improved binding activity have not been described.

Thus, the technical problem underlying the present invention is to provide sgp130 muteins with improved binding activity, which can be used to construct therapeutic sgp130 polypeptides or dimers, e.g. sgp130Fc, with higher biological activity, and, thus, a higher therapeutic efficacy, lower effective therapeutic doses and lower cost of goods in pharmaceutical production.

The solution of said technical problem is achieved by providing the embodiments characterized in the claims. Three amino acid residues (Thr$_{102}$, Gln$_{113}$ and Asn$_{114}$) of the N-terminal Ig-like domain of gp130, which point into the unknown interaction area described above, were chosen for mutagenesis in order to detect potential stronger interactions (see mutation scheme in FIG. 1). Surprisingly, a significant additive increase in binding activity and affinity was discovered with three decidedly non-conservative amino acid exchanges (Thr$_{102}$ mutated to Tyr$_{102}$, abbreviated Thr102Tyr or T102Y;

Gln$_{113}$ mutated to Phe$_{113}$, abbreviated Gln113Phe or Q113F; or Asn$_{114}$ mutated to Leu$_{114}$, abbreviated Asn114Leu or N114L), indicating that the wild type interaction site had only evolved to a far suboptimal affinity level for the IL-6/(s)IL-6R complex. As gp130 binds multiple and diverse ligands, this may be the result of a structural compromise evolved to accommodate all ligands. Moreover, the effect of the mutations described in the present invention is demonstrated to be specific for the human IL-6/(s)IL-6R/gp130 structures.

BRIEF DESCRIPTION OF THE DRAWINGS

FIG. 1: Muteins of the N-Terminal Domain of gp130
The amino acid residues Thr$_{102}$, Gln$_{113}$ and Asn$_{114}$ of the N-terminal immunoglobulin (Ig)-like domain of gp130 (SEQ ID NO:2) were mutated. The non-conservative changes Thr$_{102}$ to Tyr$_{102}$ (mutation T102Y) (SEQ ID NO:3), Gln$_{113}$ to Phe$_{113}$ (mutation Q113F) (SEQ ID NO:4) and Asn$_{114}$ to Leu$_{114}$ (mutation N114L) (SEQ ID NO:5) both alone and in combination (SEQ ID NOS:6-10) improved the binding activity of sgp130Fc dimers (see FIG. 3).

FIG. 2: Silver-Stained Native Polyacrylamide Gel with Protein Preparations of Wild Type and Mutein sgp130Fc Dimers
Compared to wild type sgp130Fc, none of the mutations showing improved binding activity increased aggregate (side product) formation. Representative data for the three single muteins (termed Thr102Tyr or T102Y; Gln113Phe or Q113F; Asn114Leu or N114L), one double mutein (Thr102Tyr/Gln113Phe or T102Y/Q113F) and the triple mutein (Thr102Tyr/Gln113Phe/Asn114Leu or T102Y/Q113F/N114L) are shown.

FIG. 5: Kinetic Constants and Affinities of Hyper-IL-6 Binding to Wild Type sgp130Fc and to the Triple Mutein T102Y/Q113F/N114L Kinetic constants were determined using surface plasmon resonance in a ProteOn XPR36 protein interaction array system (Bio-Rad).

Figure 3A:
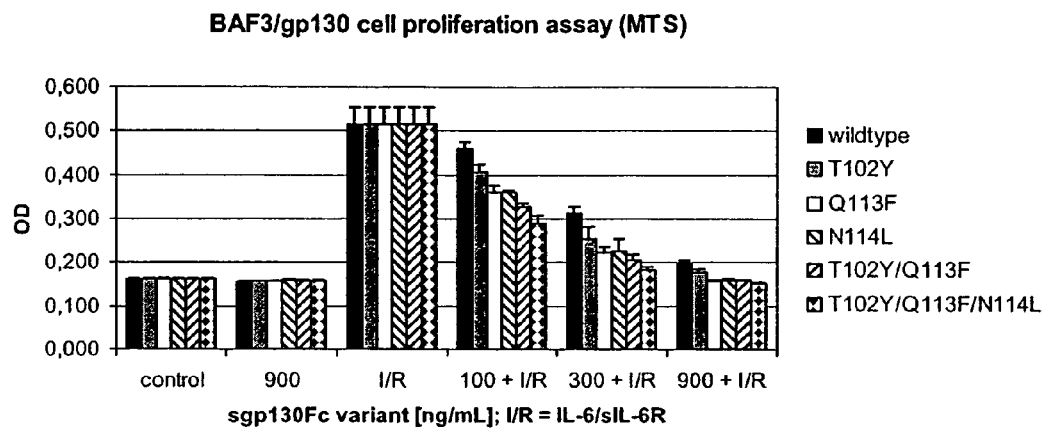
FIG. 3: Inhibition of IL-6/sIL-6R-induced Proliferation of BAF3/gp130 cells by wild type and mutein sgp130Fc dimers
The sgp130Fc muteins are significantly more biologically active than wild type sgp130Fc in blocking BAF3/gp130 cell proliferation triggered by 100 ng/mL IL-6 plus 50 ng/mL sIL-6R (A) or 1 ng/mL Hyper-IL-6 (B). The IC$_{50}$ of the triple mutein Thr102Tyr/Gln113Phe/Asn114Leu (T102Y/Q113F/N114L) is at least 3-fold lower than the wild type IC$_{50}$ in all assays.
(A) Colorimetric MTS assay.
(B) Fluorometric Cell Titer-Blue assay with higher sensitivity to illustrate consistency of the differential activity between sgp130Fc muteins over almost three orders of magnitude. Abbreviations and symbols: Cell Titer-Blue, fluorescent resorufin (excitation at 530 nm, emission at 590 nm) as the cell metabolic conversion product of the resazurin Cell Titer-Blue substrate; IC$_{50}$, concentration with 50% inhibitory efficacy; IL-6, interleukin-6; I/R, IL-6 plus sIL-6R; MTS, substrate which is converted by metabolically active cells to a soluble formazan product absorbing at 490 nm; OD, optical density at 490 nm; sIL-6R, soluble interleukin-6 receptor.

Thus, the present invention relates to a polypeptide capable of inhibiting the activity of the agonistic complex IL-6/sIL-6R and comprising the entire extracellular part of glycoprotein gp130 or variants or fragments thereof, wherein at least one of the three amino acid residues Thr$_{102}$, Gln$_{113}$ or Asn$_{114}$ of the N-terminal Ig-like domain of gp130 is substituted by a different amino acid residue. These muteins of the complete extracellular domain of gp130 or variants or fragments thereof are present as soluble monomers or dimers capable of inhibiting the agonistic complex IL-6/sIL-6R with superior binding activity compared to wild type soluble gp130, and can be fused directly or via polypeptide linkers to an Fc domain of an immunoglobulin heavy chain or other tags.

In a preferred embodiment of the polypeptide of the present invention,
(a) Thr$_{102}$ is substituted by a large neutral amino acid residue, e.g., Tyr, Trp, Leu, Ile, Phe or Met;
(b) Gln$_{113}$ is substituted by a hydrophobic and nonpolar amino acid residue, e.g., Phe, Trp, Ile, Leu, Met, Val or Ala; and/or
(c) Asn$_{114}$ is substituted by a hydrophobic and nonpolar amino acid residue, e.g., Phe, Trp, Ile, Leu, Met, Val or Ala.

In a more preferred embodiment, the soluble gp130 mutein of the present invention comprises at least one of the following mutations in the N-terminal Ig-like domain of gp130: Thr$_{102}$ mutated to Tyr$_{102}$ (abbreviated Thr102Tyr or T102Y), Gln$_{113}$ mutated to Phe$_{113}$ (abbreviated Gln113Phe or Q113F) or Asn$_{114}$ mutated to Leu$_{114}$ (abbreviated Asn114Leu or N114L).

The term "soluble" as used herein refers to a gp130 polypeptide lacking the intracellular domain and, preferably, the transmembrane domain.

The soluble gp130 (sgp130) monomers or dimers of the present invention may be engineered using known methods. The domains utilized may consist of the entire extracellular domain of gp130 or they may consist of further variants or fragments thereof that maintain the ability to inhibit the activity of the agonistic complex IL-6/sIL-6R. Preferred fragments are fragments consisting at least of the extracellular domains D1 to D3.

Even more preferred embodiments of the sgp130 mutein of the present invention comprise one of the two mutations Gln113Phe (Q113F) or Asn114Leu (N114L).

In a particularly preferred embodiment of the mutein of the present invention, two of the three mutations Thr102Tyr (T102Y), Gln113Phe (Q113F) or Asn114Leu (N114L) are combined, resulting in the double muteins Thr102Tyr/Gln113Phe (T102Y/Q113F), Thr102Tyr/Asn114Leu (T102Y/N114L) or Gln113Phe/Asn114Leu (Q113F/N114L).

In the most preferred embodiment of the mutein of the present invention, all three mutations Thr102Tyr (T102Y), Gln113Phe (Q113F) and Asn114Leu (N114L) are combined, resulting in the triple mutein Thr102Tyr/Gln113Phe/Asn114Leu (T102Y/Q113F/N114L).

Moreover, mutated sgp130 polypeptides are preferred, wherein the polypeptide is fused directly or via a polypeptide linker to a tag. The term "tag" means any naturally occurring or artificial polypeptide or other molecular structure, which allows purification and/or detection of the mutated sgp130 polypeptide and/or further improves the pharmacodynamic and/or pharmacokinetic properties of the mutated sgp130 polypeptide. Polypeptide linkers may be entirely artificial (e.g., comprising 2-50 amino acid residues independently selected from the group consisting of glycine, serine, asparagine, threonine and alanine) or adopted from naturally occurring proteins.

In a further preferred embodiment of the sgp130 muteins of the present invention, one or more N-glycosylation sites are inserted between the sgp130 mutein, variant or fragment thereof and a tag (e.g., an immunoglobulin Fc domain), and/or between the sgp130 mutein and a linker, and/or between the linker and the tag. Amino acid motifs of N-glycosylation sites with the core sequence Asn-X-Ser or Asn-X-Thr depend on the context of the motif in the protein and can be predicted and designed by the person skilled in the art, e.g. by using free software such as NetNGlyc (Center for Biological Sequence Analysis, Technical University of Denmark). A preferred N-glycosylation linker element for muteins of the invention is His-Asn-Leu-Ser-Val-Ile (SEQ ID NO:1).

Another object of the present invention are PEGylated or other chemically modified forms of the sgp130 mutein, variant, fragment or fusion construct thereof. PEGylation of the sgp130 molecules can be carried out, e.g., according to the methods described for human IFN-α, IFN-β, IL-15 or IL-2 (Youngster et al. (2002) Curr. Pharm. Des. 8:2139-57; Grace et al. (2001) J. Interferon Cytokine Res. 21:1103-15; Pepinsky et al. (2001) J. Pharmacol. Exp. Ther. 297:1059-66; Pettit et al. (1997) J. Biol. Chem. 272:2312-8; Goodson et al. (1990) Biotechnology 8:343-6; Katre (1990) J. Immunol. 144:209-13).

Any kind of polyethylene glycol is suitable for the present invention provided that the PEG-polypeptide or PEG-polypeptide-dimer is still capable of blocking IL-6 responses dependent on sIL-6R which can be assayed according to methods known in the art. Preferably, the polyethylene glycol of the polypeptide or polypeptide-dimer of the present invention is PEG 1000, 2000, 3000, 5000, 10000, 15000, 20000 or 40000 with PEG 20000 or 40000 being particularly preferred.

In order to form a dimer, two sgp130 muteins, variants, fragments or fusion constructs thereof are linked to each other through a simple covalent bond, a flexible peptide linker or, preferably, via one or more disulfide bridges. Peptide linkers may be entirely artificial (e.g., comprising 2-50 amino acid residues independently selected from the group consisting of glycine, serine, asparagine, threonine and alanine) or adopted from naturally occurring proteins. Disulfide bridge formation can be achieved, e.g., by recombinant expression as an immunoglobulin Fc fusion protein, wherein the nucleic acid sequence encoding the sgp130Fc monomer contains one or more cysteine encoding codons, preferably in the hinge region of the Fc domain.

The present invention also relates to polypeptide dimers as described above, wherein the polypeptide is fused to an Fc domain of an immunoglobulin heavy chain. The expression "fused ( . . . ) to an Fc domain of an immunoglobulin heavy chain" comprises all immunoglobulin classes and subclasses. Preferably, the fusion partner of the sgp130 mutein consists of the Fc domain of an IgG protein, and more preferably, of an IgG1 protein. However, any Fc part may also comprise sequences from more than one immunoglobulin class or subclass, and selecting particular sequence motifs to optimize desired effector functions is within the ordinary skill in the art.

In addition to or instead of a fusion with an immunoglobulin Fc part, the gp130 extracellular domain (soluble gp130) muteins of the present invention may be fused to other naturally occurring or artificial polypeptides and/or tags, such as poly(His), Myc, Strep, polyarginine, Flag, green fluorescent protein (GFP) or engineered derivatives thereof, TAP, glutathione S-transferase (GST), HA, calmodulin-binding peptide (CBP), maltose-binding protein (MBP), V5, HSV, S, vesicular stomatitis virus (VSV), Protein C, Luciferase, Glu-Glu, E, beta-GAL, T7 or other epitopes to which antibodies or other binding molecules are available to allow rapid purification, detection, e.g. in Western blot or ELISA, immunoprecipitation, or activity depletion/blocking in bioassays.

The fusions of the sgp130 muteins, preferably at the C-terminus, or the variants or fragments thereof to the hinge region of an immunoglobulin Fc part or to other tags may be direct or they may employ a flexible polypeptide linker domain of various lengths and amino acid combinations. These linkers may be entirely artificial (e.g., comprising 2-50 amino acid residues independently selected from the group consisting of glycine, serine, asparagine, threonine and alanine) or adopted from naturally occurring proteins. Such linkers can enhance flexibility and binding properties of the mutein monomers or dimers.

The sgp130 mutein monomers and dimers of the present invention are preferably recombinantly produced by use of a polynucleotide encoding said mutein, variant, fragment or fusion construct thereof.

Thus, the present invention also relates to a polynucleotide encoding the polypeptides of the invention as well as vectors, preferably expression vectors containing said polynucleotides and host cells or cell-free expression systems containing such vectors.

For the production of the mutein monomers and dimers of the invention, the polynucleotides are obtained from existing clones, i.e., preferably encode the naturally occurring polypeptide or a part thereof (for human gp130/IL6ST: GenBank sequence NM_002184 and supporting clones; for the constant region of human immunoglobulins, e.g., IgG1/IGHG1, GenBank sequence AK057754). Polypeptides encoded by any polynucleotide which hybridises to the complement of the native DNA or RNA under highly stringent or moderate stringent conditions (for definitions, see Sambrook (1989), Molecular Cloning, A Laboratory Manual, Cold Spring Harbor Laboratory N.Y.) as long as that polypeptide maintains the biological activity of the native sequence, are also useful for producing the mutein monomers and dimers of the present invention.

The recombinant vectors can be constructed according to methods well known to the person skilled in the art; see, e.g., Sambrook (1989), Molecular Cloning, A Laboratory Manual, Cold Spring Harbor Laboratory N.Y. A variety of expression vector/host systems may be utilised to contain and express sequences encoding the sgp130 mutein, variant, fragment or fusion construct thereof of the present invention. These include, but are not limited to, cell-free expression systems, such as the in vitro wheat germ expression system; microorganisms such as bacteria transformed with recombinant bacteriophage, plasmid, or cosmid DNA expression vectors; fungi (e.g., yeast) transformed with fungal (e.g., yeast) expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

In bacterial systems, a number of expression vectors may be selected depending upon the use intended for the mutein monomers and dimers of the present invention. Vectors suitable for use in the present invention include, but are not limited to the pSKK expression vector for expression in bacteria.

In wild type or modified (e.g., glycoengineered) yeast species, such as *Saccharomyces cerevisiae, Schizosaccharomyces pombe* or *Pichia pastoris*, a number of vectors containing constitutive or inducible promoters or promoter systems such as alpha factor, alcohol oxidase, PGH, tetracycline glucose etc. may be used; for reviews, see Grant et al. (1987) Methods Enzymol. 153:516-44; Siam et al. (2004) Methods 33:189-98; Macauley-Patrick et al. (2005) Yeast 22:249-70, Gellissen et al. (2005) FEMS Yeast Res. 5:1079-96; Wildt and Gerngross (2005) Nat. Rev. Microbiol. 3:119-28.

In cases where plant expression systems are used (for review, see, e.g., Stoger et al. (2005) Curr. Opin. Biotechnol. 16:167-73; Gomord et al. (2005) Trends Biotechnol. 23:559-65), the expression of sequences encoding the muteins or variants or fragments or fusion constructs thereof of the present invention may be driven by any of a number of promoters. For example, viral promoters such as the 35S and 19S promoters of CaMV may be used alone or in combination with the omega leader sequence from TMV (Takamatsu (1987) EMBO J. 6:307-11). Alternatively, plant promoters such as the small subunit of RUBISCO or heat shock promoters may be used (Coruzzi et al. (1984) EMBO J. 3:1671-80; Broglie et al. (1984) Science 224:838-43; Winter et al. (1991) Results Probl. Cell Differ. 17:85-105). These constructs can be introduced into plant cells by direct DNA transformation or pathogen-mediated transfection. Such techniques are described in a number of generally available reviews (see, e.g., Hobbs and Murry in McGraw Hill Yearbook of Science and Technology (1992) McGraw Hill, New York, N.Y.; pp. 191-6).

An insect cell system may also be used to express the mutein monomers and dimers of the present invention. For example, in one such system, *Autographa californica* nuclear polyhedrosis virus (AcNPV) is used as a vector to express foreign genes in *Spodoptera frugiperda* cells or in *Trichoplusia larvae*. The sequences may be cloned into a non-essential region of the virus, such as the polyhedrin gene, and placed under control of the polyhedrin promoter. Successful insertion of the DNA sequence encoding the sgp130 muteins or fragments or variants or fusion constructs thereof, e.g. for a sgp130Fc fusion protein, will render the polyhedrin gene inactive and produce recombinant virus lacking coat protein. The recombinant viruses may then be used to infect, e.g., *S. frugiperda* cells or *Trichoplusia larvae* in which the sgp130 mutein monomers and dimers of the present invention may be expressed (Engelhard et al. (1994) Proc. Nat. Acad. Sci. U.S.A. 91:3224-7).

In mammalian host cells, a number of expression systems based, e.g., on lipid-based transfection or viral transduction of the cells may be utilised. In cases where an adenovirus is used as an expression vector, sequences encoding the sgp130 muteins or fragments or variants or fusion constructs thereof of the present invention may be ligated into an adenovirus transcription/translation complex consisting of the late promoter and tripartite leader sequence. Insertion in a non-essential E1 or E3 region of the viral genome may be used to obtain a viable virus which is capable of expressing the mutein monomers and dimers of the present invention in infected host cells (Logan and Shenk (1984) Proc. Natl. Acad. Sci. U.S.A. 81:3655-9). In addition, transcription enhancers, such as the Rous sarcoma virus (RSV) enhancer, may be used to increase expression in mammalian host cells.

After the introduction of the recombinant vector(s), the host cells are grown in a selective medium, which selects for the growth of vector-containing cells. Any number of selection systems may be used to recover transformed cell lines. These include, but are not limited to, the herpes simplex virus thymidine kinase (Wigler et al. (1977) Cell 11:223-32) and adenine phosphoribosyltransferase (Lowy et al. (1980) Cell 22:817-23) genes which can be employed in tk.sup.- or aprt-.sup.-cells, respectively. Also, antimetabolite, antibiotic or herbicide resistance can be used as the basis for selection; e.g., dhfr which confers resistance to methotrexate (Wigler et al. (1980) Proc. Natl. Acad. Sci. U.S.A. 77:3567-70); npt, which confers resistance to the aminoglycosides neomycin and G-418 (Cölbere-Garapin et al. (1981) J. Mol. Biol. 150: 1-14); and als or pat, which confer resistance to chlorsulfuron and phosphinotricin acetyltransferase, respectively. Additional selectable genes have been described, e.g., trpB, which allows cells to utilise indole in place of tryptophan, or hisD, which allows cells to utilise histinol in place of histidine (Hartman and Mulligan (1988) Proc. Natl. Acad. Sci. U.S.A. 85:8047-51). The use of visible markers has gained popularity with such markers as anthocyanins, beta-glucuronidase and its substrate GUS, and luciferase and its substrate luciferin, being widely used not only to identify transformants, but also to quantify the amount of transient or stable protein expression attributable to a specific vector system (Rhodes et al. (1995) Methods Mol. Biol. 55:121-31).

Purification of the recombinant polypeptides is carried out by any one of the methods known for this purpose, i.e., any conventional procedure involving extraction, precipitation, chromatography, electrophoresis, or the like. A further purification procedure that may be used is affinity chromatography using, e.g., Protein A, Protein G or monoclonal antibodies, which bind the target polypeptide(s) and which are produced and immobilized on a gel matrix contained within a column. Impure preparations containing the recombinant polypeptide are passed through the column. The polypeptide will be bound to the column by the specific interaction with the affinity gel matrix while the impurities will pass through. After washing, the polypeptide is eluted from the gel by a change in pH or ionic strength and then, if it is produced as the monomer, dimerized and, if desired, PEGylated.

Accordingly, the present invention also relates to a method of producing the sgp130 mutein monomers and dimers of the present invention, comprising a cell-free expression system or culturing a host cell transformed with a DNA sequence encoding a sgp130 mutein or fragment or variant or fusion construct thereof and recovering the mutein monomer or dimer from said system, host cell or the culture.

The sgp130 mutein monomers and dimers of the present invention are useful in the treatment and/or prevention of all the pathologies, in which the activity of the agonistic complex IL-6/sIL-6R should be inhibited. Thus, the present invention also relates to a pharmaceutical composition containing an effective amount of sgp130 mutein monomers or dimers of the present invention, preferably combined with a pharmaceutically acceptable carrier. "Pharmaceutically acceptable" is meant to encompass any carrier, which does not interfere with the effectiveness of the biological activity of the active ingredient and that is not toxic to the host to which it is administered. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods and can be administered to the subject at an effective dose.

An "effective amount" refers to an amount of the active ingredient that is sufficient to affect the course and the severity of the disease, leading to the prevention, reduction or remission of such pathology.

An effective dose useful for treating and/or preventing these diseases or disorders may be determined using methods known to one skilled in the art (see, e.g., Fingl et al., The Pharmocological Basis of Therapeutics, Goodman and Gilman, eds. Macmillan Publishing Co., New York, pp. 1-46 (1975)).

Administration of the compositions may be effected by different ways, e.g. by intravenous, intraarterial, intraperitoneal, subcutaneous, intramuscular, intraarticular, peroral, pulmonal, inhalative, nasal, rectal, vaginal, topical or intradermal administration. The dosage regimen will be determined by the attending physician and other clinical factors. As is well known in the medical arts, dosages for any one patient depend on many factors, including the patient's size, body surface area, age, sex, the particular compound to be administered, time and route of administration, the kind of therapy, general health and other drugs being administered concurrently.

The present invention also relates to the use of sgp130 mutein monomers and dimers as defined above for the preparation of a pharmaceutical composition for the treatment and/or prevention of a disease or disorder where blockage of the agonistic complex IL-6/sIL-6R has a beneficial effect.

Preferred medical uses of the mutein monomers and dimers of the present invention are the treatment/prevention of bone resorption, hypercalcemia, cachexia, tumors or other types of cancer (e.g., colon cancer, multiple myeloma, lymphoma, leukaemia, Hodgkin's disease or Castleman's disease), autoimmune diseases (e.g., multiple sclerosis, type 1 diabetes or lupus erythematosus), inflammatory or atopic diseases (e.g., Crohn's disease, ulcerative colitis, rheumatoid arthritis, juvenile rheumatoid arthritis, asthma, psoriasis, sarcoidosis, lupus erythematosus, uveitis or allergic conjunctivitis), infections (e.g., by bacteria, viruses, fungi or other pathogens), sepsis, as well as endocrinologic disorders and metabolic or catabolic diseases (e.g., type 2 diabetes, obesity, hyperglycemia or hypercholesterinemia).

Finally, the present invention provides an antibody that is capable of binding to a polypeptide of the present invention and which is specific for the mutated peptide motif(s) or the specific linker region of said polypeptide. The term "antibody" used in this context, preferably, relates to distinct monoclonal antibody preparations. Monoclonal antibodies are made against (a) mutated peptide motif(s) or the specific linker region of said polypeptide by using appropriate fragments of these peptides/polypeptides as an antigen by methods well known to those skilled in the art (see, e.g., Köhler et al. (1975) Nature 256:495-7). As used herein, the term "antibody" (Ab) or "monoclonal antibody" (Mab) is meant to include intact molecules as well as antibody fragments (such as, e.g., Fab and F(ab')2 fragments) which are capable of specifically binding to proteins. Fab and $F(ab')_2$ fragments lack the Fc fragment of intact antibodies, clear more rapidly from the circulation, and may have less non-specific tissue binding than an intact antibody (Wahl et al. (1983) J. Nucl. Med. 24:316-25). Thus, these fragments are preferred, as well as the products of an Fab or other immunoglobulin expression library. Moreover, antibodies of the present invention include chimeric, single chain, and humanized antibodies. Such antibodies might be useful for different purposes, e.g., allow rapid purification, detection, e.g. in Western blot or ELISA, immunoprecipitation, or activity depletion/blocking in bioassays.

Thus, the present invention also relates to a diagnostic method which is based on the detection of the specific binding of an antibody of the invention to a polypeptide of the invention.

The examples below explain the invention in more detail.

EXAMPLE 1

Construction and Production of sgp130Fc Muteins (A) Material

The Gateway cloning system components (AccuPrime Pfx DNA Polymerase, the donor vector pDONR221, the CMV promoter-controlled expression vector pcDNA-DEST40, BP and LR recombinase for insert transfer and competent E. coli cells) were purchased from Invitrogen (Karlsruhe, Germany). QuikChange II and QuikChange Multi site-directed mutagenesis kits were obtained from Stratagene (Amsterdam, The Netherlands). PAGE purified mutagenesis primers were from Microsynth (Balgach, Switzerland). CHO-K1 cells were obtained from the German Collection of Microorganisms and Cell Cultures (Braunschweig, Germany). Culture medium components were purchased as follows: Ham's F12 medium, low IgG FBS and Dulbecco's PBS (PAA Laboratories; Cölbe, Germany), FBS (Biochrom; Berlin, Germany), Trypsin/EDTA solution (Invitrogen) and G418 solution (Sigma-Aldrich; Taufkirchen, Germany). The transfection reagent Lipofectamine 2000 was from Invitrogen. Santa Cruz (Heidelberg, Germany) supplied Protein A/G Plus Agarose for immunoprecipitation. For primary detection in Western blots, a mouse anti-human IgG (Fc) monoclonal antibody was used (CBL102; Chemicon; Hofheim, Germany). Western blot secondary detection was performed with an anti-mouse IgG HRP-linked antibody, ECL-Plus Western blotting substrate and Hyperfilm ECL (all from GE Healthcare; Munich, Germany). Roller bottles (2.1 L, 2.5× surface) were purchased from Greiner Bio-One (Frickenhausen, Germany). Cellulose acetate filters (0.45 µm) for a vacuum filter unit were purchased from Sartorius (Göttingen, Germany). MabSelect protein A affinity matrix (product code 17-5199-01) in a XK16/20 column and PD-10 desalting columns were obtained from GE Healthcare (Munich, Germany). Amicon Ultra-15 50 kDa Ultracel-PL membrane concentration units were purchased from Millipore (Eschborn, Germany). Ready-made acrylamide-bis solution (19:1, 30%) for PAGE was supplied by Bio-Rad (Munich, Germany).

(B) Construction of sgp130Fc Muteins

A cDNA for full-length sgp130Fc comprising the complete extracellular domain of gp130 and the wild type human IgG1 Fc (sources: for human gp130/IL6ST: GenBank sequence NM_002184 and supporting clones; for the constant region of human IgG1/IGHG1: e.g., GenBank sequence AK057754) was synthesized and codon-optimized for expression in CHO-K1 cells and subcloned into pDONR221 using Gateway primers, AccuPrime Pfx DNA Polymerase and BP recombinase in a standard Gateway cloning procedure. The subcloned insert was completely sequence-verified using stacked forward and reverse sequencing primers every 250-300 bp. In multiple site-directed mutageneses using the QuikChange Multi and QuikChange II kits, the three gp130 amino acid residues $Thr_{102}$, $Gln_{113}$ and $Asn_{114}$ were mutated according to the mutation scheme depicted in FIG. 1. Mutated clones were verified by complete sequencing as described above. Subsequently, the insert was transferred to the expression vector pcDNA-DEST40 by Gateway LR recombination. As the insert encodes two stop codons after the Fc part, the tags coded in pcDNA-DEST40 (V5 and 6×His epitopes) are not present in the muteins. Positive clones were identified by AlwNI restriction digest and sequence verified again.

(C) Cell Culture and Transfection

CHO-K1 cells were grown in Ham's F12 medium supplemented with 10% FBS at 37° C. and 5% $CO_2$ in a water-saturated atmosphere. Maintenance cultures were split every 3-4 days and used only up to 20 passages. Cells were transfected with the expression constructs using Lipofectamine 2000 and standard conditions for CHO-K1 supplied by Invitrogen. For a first transient expression test, CHO-$K^1$ cells were transfected in 6-well plates, and both cells and supernatants were harvested 24 h after transfection. sgp130Fc or sgp130Fc muteins were immunoprecipitated from the supernatants using Protein A/G Plus Agarose according to the manufacturer's instructions. Whole cell protein was extracted and Western blots with anti-human IgG (Fc) antibody were performed with the cell lysates and immunoprecipitates as described in Waetzig et al. (2002) J. Immunol. 168:5342-51.

(D) Production of sgp130Fc and sgp130Fc Muteins in CHO-K1 Cells

After successful transient expression, CHO-K1 cells were transfected and positive clones were selected using 400 μg/mL G418 in 10 cm cell culture plates. To determine product quality and properties, a pre-selected polyclonal CHO-K1 pool was transferred to roller bottles and cultured with low IgG FBS. Supernatants of the confluent cells were harvested 3 times a week, centrifuged for 20 min at 500×g and 4° C. to remove cells and 40 min at 3,500×g and 4° C. to remove debris, and were then either processed immediately or frozen at −80° C. In parallel, stable cell clones were selected from the pre-selected pool using a limited dilution method and characterized by Western blot expression analysis as described above. Clones with the highest and most stable expression were transferred to roller bottles and used for permanent production.

(E) Affinity Chromatography Purification and Quality Control sgp130Fc- or sgp130Fc mutein-containing supernatants from roller bottle cultures were purified at 4° C. using a P-1 peristaltic pump and an ÄKTA Purifier 100 System (both from GE Healthcare; Munich, Germany). The protocol was based on the manufacturer's recommendations for the purification of monoclonal antibodies. After centrifugation, the pH of the fresh or thawed (on ice) supernatant was adjusted to 6.7-7.0. After two rounds of vacuum filtration (0.45 μm) the supernatant was degassed and—if necessary—the pH was adjusted again to a value of 6.7-7.0. Subsequently, the PBS-equilibrated affinity chromatography column (10 mL MabSelect in a XK16/20 column) was loaded with 2-4 L of supernatant at a flow rate of 3-10 mL/min using the P-1 pump. After washing with PBS, the column was transferred to the ÄKTA purifier and washed again with PBS until the $A_{280}$ stabilized after quantitative removal of unbound protein. For the elution, the ÄKTA system was equipped with two 50 mM sodium citrate buffers at pH 3.25 and 5.5, respectively, which were mixed to produce the desired pH conditions (pH 3.7 for elution of sgp130Fc and the sgp130Fc muteins). Fractions of 10 mL were collected in 15 mL tubes containing 2 mL of 1 M Tris-HCl (pH 11). The peak fractions were pooled, and the pH was measured and adjusted to 7.5, if necessary. Pool protein concentration was measured by $A_{280}$ and the pool was concentrated to 2-5 mg/mL using Amicon Ultra-15 50 kDa Ultracel-PL membrane concentration units. PBS-equilibrated PD-10 desalting columns were used to replace the citrate buffer with PBS, followed by another protein concentration measurement at 280 nm. Samples were obtained for quality control and analysed by native or denaturing polyacrylamide gel electrophoresis (7.5%) and subsequent silver staining (FIG. 2). Final pool protein concentrations were measured and set to 2-3 mg/mL in PBS, and single-use aliquots were frozen at −80° C. for long-term storage.

(F) Results

Purifiability of sgp130Fc mutein dimers did not differ from wild type sgp130Fc. As shown in FIG. 2, the quality and amount of aggregates was not significantly influenced by the point mutations (only representative muteins of the present invention are shown, cf. FIG. 1).

EXAMPLE 2

Bioactivity of sgp130Fc Muteins in a Standardized Cell Proliferation Assay (A) Material The stably transfected B cell precursor cell line BAF3/gp130 was maintained using Hyper-IL-6 (a designer cytokine consisting of covalently linked IL-6 and sIL-6R; Fischer et al. (1997) Nat. Biotechnol. 15:142-5). DMEM cell culture medium and Dulbecco's PBS were purchased from PAA Laboratories (Cölbe, Germany), FBS was from Biochrom (Berlin, Germany). Interleukin-6 (IL-6) and soluble interleukin-6 receptor (sIL-6R) were obtained from BioSource (Solingen, Germany) and R&D Systems (Wiesbaden, Germany), respectively. The colorimetric Cell Titer 96 Aqueous Non-Radioactive Cell Proliferation Assay (MTS) and the fluorometric Cell Titer-Blue Cell Viability Assay were both obtained from Promega (Mannheim, Germany) and performed according to the manufacturer's instructions.

(B) Blockage of IL-6/sIL-6R-induced BAF3/gp130 Cell Proliferation by sgp130Fc or sgp130Fc Muteins BAF3/gp130 cells depend on the presence of the IL-6/sIL-6R complex or Hyper-IL-6 in the culture medium for proliferation and viability. For maintenance, BAF3/gp130 cells were cultured at a density of less than $5\times10^5$ cells/mL in DMEM with 10% FBS and 10 ng/mL Hyper-IL-6. The 10 ng/mL Hyper-IL-6 could be replaced by 100 ng/mL IL-6 plus 50 ng/mL sIL-6R. Cells were passaged twice a week. For assays, cells were washed twice in medium without Hyper-IL-6 (or IL-6/sIL-6R) and were then seeded at 5,000 cells/well in 96-well plates. Wild type sgp130Fc or sgp130Fc muteins were added at various concentrations ranging from 900 to 10 ng/mL (1:3 or 1:10 dilution series; FIG. 3). Subsequently, cells were incubated for 3 days in the presence of 100 ng/mL IL-6 and 50 ng/mL sIL-6R or 1 ng/mL Hyper-IL-6. Controls included unstimulated cells without and with the maximum concentration of sgp130Fc or sgp130Fc muteins as well as cells which were only incubated with IL-6 and sIL-6R (FIG. 3).

(C) Results

Figure 3B:
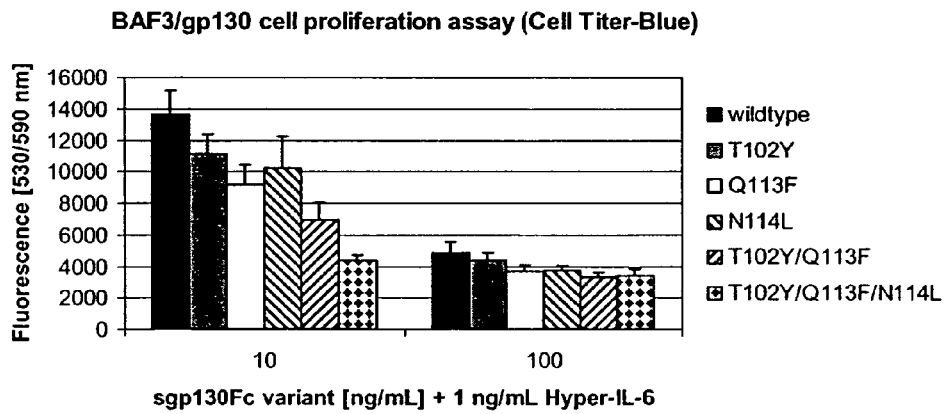

The biological activity of wild type sgp130Fc or sgp130Fc muteins in the cell culture was measured by the reduction of the number of viable BAF3/gp130 cells after 3 days (as determined by conversion of the MTS substrate or Cell Titer-Blue Reagent by metabolically active cells according to the manufacturer's information). MTS substrate (FIG. 3A) and Cell Titer-Blue Reagent (FIG. 3B) cover distinct, but overlapping ranges of sensitivity, with the Cell Titer-Blue fluorescence (530 nm excitation, 590 nm emission wavelength) being one order of magnitude more sensitive. Results from both assay systems showed (1) that the binding activity of a mutein containing the single mutation Thr102Tyr (T102Y) was superior to wild type, but inferior to muteins containing a single mutation of either Gln113Phe (Q113F) or Asn114Leu (N114L), (2) that a combination of two mutations from the group of Thr102Tyr (T102Y), Gln113Phe (Q113F) or Asn114Leu (N114L) was superior to any single mutation (as an example, the double mutein Thr102Tyr/Gln113Phe (T102Y/Q113F) is shown in FIG. 3) and (3) that combining all three mutations in the triple mutein Thr102Tyr/Gln113Phe/Asn114Leu (T102Y/Q113F/N114L) leads to optimal binding activity (FIG. 3). The $IC_{50}$ of the triple mutein is at least 3-fold lower than the wild type $IC_{50}$ in all assays. This indicates that the mutein T102Y/Q113F/N114L could be used at less than one third of the therapeutic concentration of the wild type compound.

EXAMPLE 3

Comparison of wild type sgp130Fc and the Triple Mutein T102Y/Q113F/N114L in an Acute Phase Response Cell Assay (A) Material HepG2 cells were obtained from DSMZ (Braunschweig, Germany). Hyper-IL-6 (a designer cytokine consisting of covalently linked IL-6 and sIL-6R; Fischer et al. (1997) Nat. Biotechnol. 15:142-5) was produced as described previously. DMEM high glucose culture medium and Dulbecco's PBS were purchased from PAA Laboratories (Cölbe, Germany), FBS was from Biochrom (Berlin, Germany). Maxisorp ELISA plates were obtained from Nunc (Wiesbaden, Germany). Anti-haptoglobin antibodies were from Lee Biosolutions (St. Louis, Mo., USA), goat anti-rabbit-POD antibody was from Pierce (Rockford, Ill., USA), and BM blue POD substrate was from Roche (Mannheim, Germany). All other chemicals were purchased from VWR/Merck (Darmstadt, Germany).

(B) Cell Culture and Haptoglobin ELISA

The human hepatoma cell line HepG2 was cultured in DMEM high glucose culture medium supplemented with 10% FBS. An ELISA for the human acute phase protein haptoglobin was performed as described previously (Oppmann et al. (1996) J. Immunol. Methods 195:153-9). Briefly, $10^5$ HepG2 cells per well were seeded in 96-well plates and left to adhere overnight. Cells were washed twice with PBS (37° C.) and starved in DMEM without FBS for 2 h. In the meantime, wild type sgp130Fc or mutein T102Y/Q113F/N114L were diluted, mixed with 5 ng/mL Hyper-IL-6 in DMEM without FBS and placed in the incubator for at least 30 min. Subsequently, the HepG2 cells were incubated with 200 µL of this mixture for 20 h, and the relative amount of haptoglobin in the cell supernatant was measured by ELISA. ELISA plates were coated with goat anti-haptoglobin antibody in carbonate buffer pH 9.0 at 1:1,000 overnight and blocked in 5% FBS in PBS for 2 h at room temperature. Samples were diluted 1:10 in blocking solution, and 100 µL/well were incubated for 1 h at room temperature. After 4 washes with PBS with 0.05% Tween 20 (PBST), 100 µL of rabbit anti-haptoglobin antibody diluted 1:1,000 in blocking solution were added and incubated at 37° C. for 30 min. After 4 washes with PBST, 100 µL goat anti-rabbit-POD antibody at 1:30,000 in blocking solution were added and incubated at 37° C. for 30 min. Following 4 washes with TBST, 100 µL BM blue POD substrate were added, and the color development was finally stopped with 1 M $H_2SO_4$. Plates were read at 450 nm, and each value was determined in quadruplicate.

(C) Results

Figure 4:
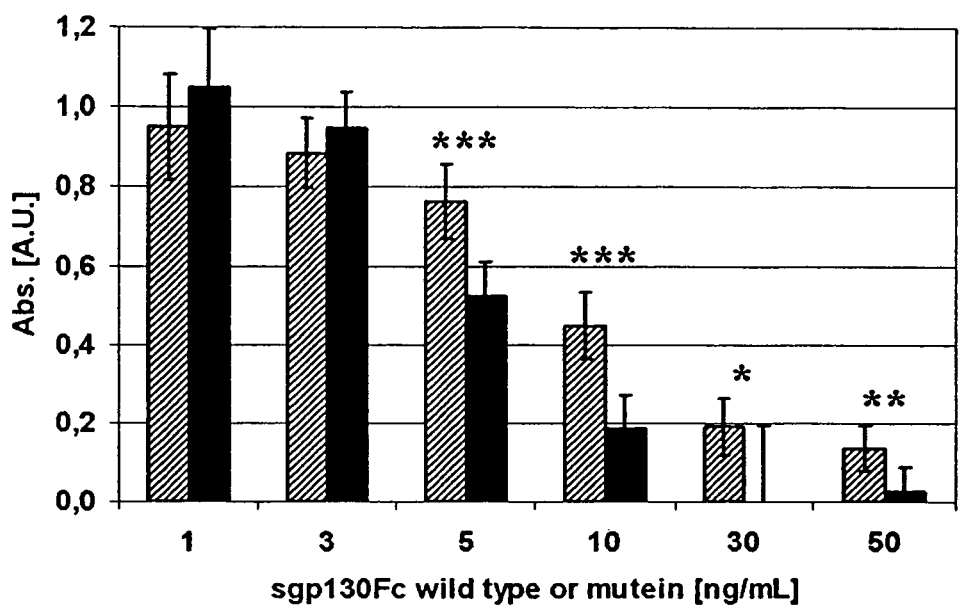
FIG. 4: Inhibition of the Acute Phase Response in a Cell Assay by Wild Type sgp130Fc and Mutein T102Y/Q113F/N114L
The acute-phase response to IL-6/sIL-6R was measured by haptoglobin ELISA using supernatants of human HepG2 hepatoma cells stimulated with 5 ng/mL Hyper-IL-6. Haptoglobin secretion was dose-dependently inhibited by increasing amounts of wild type sgp130Fc (hatched) or the triple mutein T102Y/Q113F/N114L (filled), which showed significantly stronger inhibitory activity (*, p<0.001; , p<0.01; *, p<0.05). Abs. [A.U.], absorption at 450 nm.

To verify the results obtained with the BAF3/gp130 cell proliferation assay (Example 2), human HepG2 hepatoma cells were used as a second model system. Upon IL-6 stimulation (Rose-John et al. (1990) Eur. J. Biochem. 190:79-83) or stimulation with the IL-6/sIL-6R complex or Hyper-IL-6 (Peters et al. (1998) J. Immunol. 161:3575-81), HepG2 cells show an induction of acute phase proteins and can be used as a model system for the response to liver inflammatory processes. The acute phase protein haptoglobin secreted by these cells in response to Hyper-IL-6 was quantified by ELISA (Oppmann et al. (1996) J. Immunol. Methods 195:153-9). FIG. 4 shows that the triple mutein T102Y/Q113F/N114L inhibits the Hyper-IL-6 response in a dose-dependent manner and significantly stronger than wild type sgp130Fc.

EXAMPLE 4

Kinetic Constants and Affinities of Wild Type sgp130Fc and the Triple Mutein T102Y/Q113F/N114L (A) Material Hyper-IL-6 (a designer cytokine consisting of covalently linked IL-6 and sIL-6R; Fischer et al. (1997) Nat. Biotechnol. 15:142-5) was produced as described previously. Dulbecco's PBS was purchased from PAA Laboratories (Cölbe, Germany). All other chemicals were obtained from VWR/Merck (Darmstadt, Germany).

(B) Surface Plasmon Resonance Measurements

Surface plasmon resonance experiments were performed with a ProteOn XPR36 protein interaction array system (Bio-Rad, Hercules, Calif., USA) according to the manufacturer's instructions. The running buffer was PBS with 0.005% Tween 20 pH 7.4 (PBST), and experiments were carried out at 25° C. The surface was activated (4 mM EDAC/1 mM sulfo-NHS) and proteins covalently coupled at 10 µg/mL in 10 mM acetate buffer pH 4.5. The respective levels of immobilization were 1.330 RU (resonance units) for wild type sgp130Fc and 1.120 RU for the mutein T102Y/Q113F/N114L. Concentrations of Hyper-IL-6 ranged from 80 to 2.5 nM in PBST (flow rate: 100 µL/min). Association and dissociation were monitored for 60 s or 600 s, respectively. Each sensogram set was referenced using the reference channel and was baseline-aligned. Sensograms were analyzed using the ProteOn Manager 2.0 software.

(C) Results

In order to examine whether the improved biological activity (see Examples 2 and 3) of the muteins exemplified by the triple mutein T102Y/Q113F/N114L is reflected in the binding kinetics, surface plasmon resonance were performed to quantify the $k_{on}$- and $k_{off}$-rates. Wild type sgp130Fc or T102Y/Q113F/N114L mutein proteins were immobilized on the affinity-sensor chip and binding of Hyper-IL-6 (representing the IL-6/sIL-6R complex) was measured. From the sensograms, the $k_{on}$ and $k_{off}$ constants and the affinity constants $K_D$ were calculated. The higher inhibitory capacity of mutein T102Y/Q113F/N114L is reflected in a similar $k_{on}$ and lower $k_{off}$ and, consequently, in a 4-fold increased affinity constant $K_D$. The change in the $k_{off}$ results from an energetically more stable complex, whereas the complex formation is only slightly affected compared to wild type sgp130Fc.

EXAMPLE 5

Molecular Modeling of a Complex of Murine IL-6/sIL-6R and Human gp130 and Hypothesis Testing in a Cell Assay (A) Modeling A model of the murine IL-6/murine IL-6R/human gp130 complex was build using the structure of the human IL-6/IL-6R/gp130 complex as a template (Boulanger et al. (2003) Science 300:2101-4). According to the published alignment, amino acid residues of IL-6 and IL-6R were exchanged in the template (Grötzinger et al. (1997) Protein Struct. Funct. Genet. 27:96-109). Insertions and deletions in the molecules were modeled using a database-search approach (Vriend (1990) J. Mol. Graph. 8:52-6).

(B) Material and Method of the Cell Assay

The standardized BAF/gp130 cell proliferation assay is described in Example 2. Murine IL-6 and sIL-6R were purchased from R&D Systems (Wiesbaden, Germany) and added to the cells at 300 ng/mL (IL-6) and 150 ng/mL (sIL-6R).

(C) Results

Figure 6:
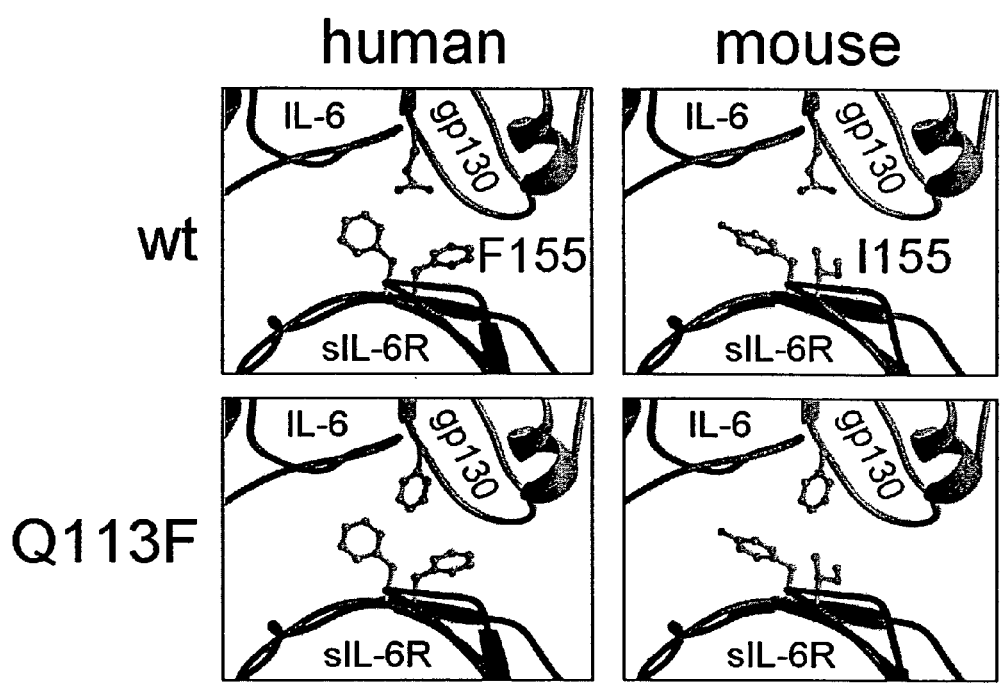
FIG. 6: Molecular Modeling of the Interaction Site of gp130, IL-6 and sIL-6R in an All-Human or a Mouse/Human Complex
In the left panels ("human"), the interaction between human wild type (wt) gp130 and mutant Q113F with human IL-6 and human sIL-6R is shown. The right panels ("mouse") show the respective interactions with murine IL-6 and sIL-6R. In the all-human complex, an aromatic cluster is formed which is hypothesized to account for the increased affinity of muteins containing Q113F.
Figure 7:
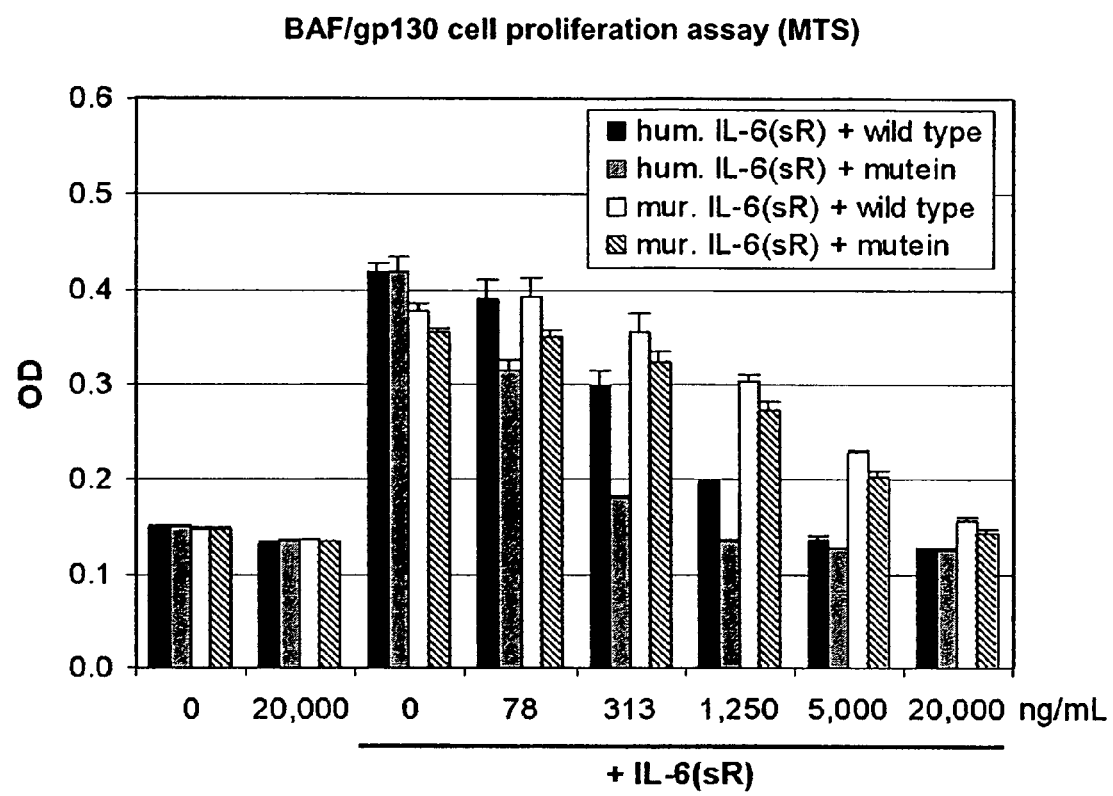
FIG. 7: Inhibition of IL-6/sIL-6R-induced Proliferation of BAF3/gp130 Cells: Comparison of Wild Type sgp130Fc and the Triple Mutein T102Y/Q113F/N114L as Well as Human and Murine IL-6/sIL-6R
Proliferation of BAF3/gp130 cells and its inhibition by wild type sgp130Fc or mutein T102Y/Q113F/N114L was measured in response to the human or murine IL-6/sIL-6R complex (MTS assay). OD, optical density at 490 nm.

In all experiments described in Examples 2-4, human IL-6 plus human IL-6 receptor or Hyper-IL-6 based on the human IL-6 and sIL-6R sequences were used. A detailed modeling of the interaction site of Q113/N114 in human gp130 suggested a cluster of hydrophobic and nonpolar amino acids as a plausible explanation for the beneficial effects observed with the mutations Q113F and N114L (FIG. 6). As a prerequisite for in vivo studies in mice, the three-dimensional structure of the human IL-6/1L-6R/gp130 complex was used to generate a model complex of murine IL-6/murine IL-6R/human gp130 for comparison. Inspection of this mouse/human complex revealed that the murine IL-6R lacks one of the aromatic residues (F155) (FIG. 6), suggesting that the enhanced binding affinity of Q113F muteins found in the all-human situation should not be observed in the mouse/human system. To test this hypothesis, we used the BAF3/gp130 standardized cell proliferation assay (with human gp130 on the BAF3 cell surface) to investigate the inhibitory activity of wild type sgp130Fc and the triple mutein T102Y/Q113F/N114L using the mouse IL-6/sIL-6R complex for stimulation. As predicted, the mutein T102Y/Q113F/N114L is not more effective than wild type sgp130Fc with murine IL-6/sIL-6R (FIG. 7). The same holds true for mutein N114L (data not shown). The increased hydrophobicity of the N114L mutations in the human system is compensated by the amino acid exchange (R117/M116) in murine IL-6 as compared to human IL-6 (data not shown). Therefore, the enhanced activity of the sgp130Fc mutein T102Y/Q113F/N114L is restricted to human IL6/sIL6R complexes. Interestingly, about 3-fold more murine IL-6/sIL-6R is needed to elicit the same proliferation signal in BAF3/gp130 cells as with human IL-6/sIL-6R, indicating that the mouse/human complex of murine IL-6/sIL-6R and human gp130 on the BAF cell surface—as well as the human gp130 contained in sgp130Fc wild type and muteins—is less efficient than its all-human counterpart.

EXAMPLE 6

In Vivo Testing of the Species-Specificity Hypothesis Using the Murine Air Pouch Model of Acute Inflammation (A) Animal Treatment All procedures involving animals and their care were conducted in accordance with national and international laws and policies as well as the guidelines for animal care of the University of Kiel (acceptance no.: V 742-72241.121-3 (20-2/04) and (76-7/00)). Mice were maintained in a 12 h light/dark cycle under standard conditions and were provided with food and water ad libitum. Blood was drawn by tail bleeding or by cardiac puncture under general anesthesia.

(B) Material

Carrageenan was obtained from Sigma-Aldrich (Taufkirchen, Germany). Dulbecco's PBS was purchased from PAA Laboratories (Cölbe, Germany). DuoSet ELISA kits for monocyte chemoattractant protein-1 (MCP-1) and sgp130 were from R&D Systems (Wiesbaden, Germany). Monoclonal antibodies Ly-6G and F4/80 were from BD Biosciences (Heidelberg, Germany) and Invitrogen (Karlsruhe, Germany), respectively.

(C) Air Pouch Model

The air pouch model of local inflammation was performed with C57B1/6 mice (Edwards et al. (1981) J. Pathol. 134:147-56). In brief, mice were anesthetized and subcutaneous dorsal pouches were created by injection of 6 ml of sterile air. After 3 days, the pouches were reinjected with 4 ml of air. On day 6, 1 ml of 1% carrageenan in sterile PBS was injected into the pouches. Wild type sgp130Fc protein or the triple mutein T102Y/Q113F/N114L (50 µg/mouse) or PBS as control were administered intraperitoneally 6 h before the carrageenan injection. Seventy-two hours after treatment, animals were sacrificed and the pouches were washed with 3 ml of PBS. The lavage fluid was immediately cooled on ice and centrifuged at 5,000 rpm for 10 min at 4° C. The supernatant was analyzed by ELISA for MCP-1 and sgp130Fc. Aliquots of the air pouch lavage fluid containing $2 \times 10^5$ cells were used for FACS analysis (FACS-Canto, Becton-Dickinson, Heidelberg, Germany). The monoclonal antibodies Ly-6G and F4/80 were used to count neutrophils and monocytes, respectively. Data were acquired from 10,000 gated events.

(D) Results

Figure 8:
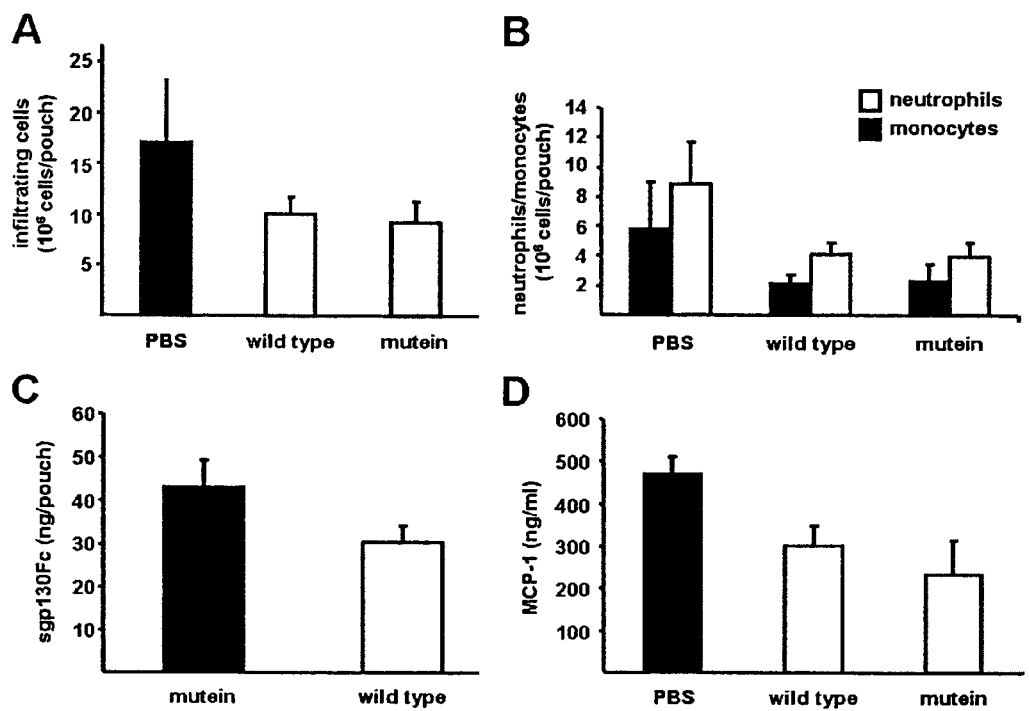
FIG. 8: Comparison of Wild Type sgp130Fc and the Triple Mutein T102Y/Q113F/N114L in the Murine Air Pouch Model of Acute Inflammation
C57Bl/6 mice were injected intraperitoneally with 10 μg of wild type sgp130Fc, 10 μg of mutein T102Y/Q113F/N114L or PBS as a carrier control 6 h before carrageenan injection. Seventy-two hours after carrageenan injection, total cell numbers (A) and numbers of neutrophils and mononuclear phagocytes (B) were determined by flow cytometry. Levels of recombinant sgp130Fc proteins (C) and the chemokine MCP-1 (D) in the inflamed air pouches were measured by ELISA. All values represent mean values±SD of 5-9 animals. MCP-1, monocyte chemoattractant protein-1.

The air pouch model was used (1) to investigate the in vivo activity of the triple mutein T102Y/Q113F/N114L and (2) to compare wild type sgp130Fc with the mutein to test the species-specificity hypothesis and to verify the in vitro data described in Example 5 in vivo. We have recently shown that in the mouse air pouch model, the IL-6/sIL-6R complex is important to drive the inflammatory process from the acute neutrophilic state to the more chronic state governed by mononuclear cells (Chalaris et al. (2007) Blood 110:1748-55; Rabe et al. (2008) Blood 111:1021-8). In this model, the infiltration of mononuclear cells is mediated by the chemokine MCP-1, which is induced in the lining cells by the IL-6/sIL-6R complex, but not by IL-6 alone. Therefore, this model was used to study whether in mice the infiltration of cells and the secretion of MCP-1 could be modulated by wild type sgp130Fc and the mutein T102Y/Q113F/N114L. Injection of both sgp130Fc proteins clearly decreased the number of infiltrating cells to the same extent (FIG. 8A). In addition, the ratio of infiltrating neutrophils and monocytes was similar (FIG. 8B). Although the concentration of the mutein T102Y/Q113F/N114L in the inflamed area was slightly higher compared to wild type sgp130Fc (FIG. 8C), the mutein T102Y/Q113F/N114L exhibits the same inhibitory effect on the concentration of MCP-1 (FIG. 8D). Therefore, the conclusion derived from our structural model (FIG. 6) and from the in vitro data (FIG. 7) is in good agreement with the situation in vivo, demonstrating that the enhanced activity of sgp130Fc mutein T102Y/Q113F/N114L is restricted to human IL-6/sIL-6R complexes.

The invention claimed is:

1. A polypeptide comprising:
   the entire extracellular part of gp130 or a fragment thereof comprising at least domains D1 to D3, which is capable of inhibiting the activity of the agonistic complex IL-6/sIL-6R, wherein domain D1 includes SEQ ID NO:2; wherein:
   $Thr_{102}$ is substituted by Tyr, Tip, Leu, Ile, Phe, or Met; and/or
   $Gln_{113}$ is substituted by Phe, Trp, Ile, Leu, Met, Val, or Ala; and/or
   $Asn_{114}$ is substituted by Phe, Tip, Ile, Leu, Met, Val, or Ala.

2. The polypeptide of claim 1, comprising at least one of the following substitutions: Thr102Tyr (T102Y), Gln113Phe (Q113F) and Asn114Leu (N114L).

3. The polypeptide of claim 2, wherein any two of the mutations Thr102Tyr (T102Y), Gln113Phe (Q113F) or Asn114Leu (N114L) are combined, resulting in double mutein Thr102Tyr/Gln113Phe (T102Y/Q113F), Thr102Tyr/Asn114Leu (T102Y/N114L), or Gln113Phe/Asn114Leu (Q113F/N114L).

4. The polypeptide of claim 2, wherein all three mutations Thr102Tyr (T102Y), Gln113Phe (Q113F) and Asn114Leu (N114L) are combined, resulting in triple mutein Thr102Tyr/Gln113Phe/Asn114Leu (T102Y/Q113F/N114L).

5. The polypeptide of claim 1, wherein the polypeptide is fused directly or via a polypeptide linker to a tag.

6. The polypeptide of claim 5, wherein the polypeptide linker is flexible and comprises 2 to 50 amino acid residues independently selected from the group consisting of glycine, serine, asparagine, threonine and alanine.

7. The polypeptide of claim 5, wherein one or more N-glycosylation sites are inserted between the polypeptide and the tag, between the polypeptide and the linker, and/or between the linker and the tag.

8. The polypeptide of claim 1, wherein said polypeptide is PEGylated.

9. A dimeric peptide comprising two polypeptides of claim 1, wherein each polypeptide is an independently selected monomer, and wherein the monomers are linked to each other through a chemical or physical linkage.

10. The dimeric peptide of claim 9, wherein the two monomers are identical.

11. A pharmaceutical composition, comprising the dimeric peptide of claim 10 and a pharmaceutically acceptable carrier.

12. The dimeric peptide of claim 9, wherein the two monomers are linked to each other by a simple covalent bond, a flexible polypeptide linker or one or more disulfide bridges.

13. The dimeric peptide of claim 9, wherein each monomer comprises the entire extracellular part of gp130.

14. A pharmaceutical composition, comprising the dimeric peptide of claim 13 and a pharmaceutically acceptable carrier.

15. A pharmaceutical composition, comprising the dimeric peptide of claim 9 and a pharmaceutically acceptable carrier.

16. The dimeric peptide of claim 9, wherein each monomer comprises a fragment comprising at least domains D1 to D3.

17. A pharmaceutical composition, comprising the dimeric peptide of claim 16 and a pharmaceutically acceptable carrier.

18. The dimeric peptide of claim 12, wherein the monomers are connected by one or more disulfide bridges, which are generated by fusing the monomer to a naturally occurring or artificial polypeptide comprising one or more free and accessible cysteine residues.

19. The dimeric peptide of claim 9, wherein each monomer is fused to an Fc domain of an immunoglobulin protein.

20. The dimeric peptide of claim 19, wherein the immunoglobulin is IgG.

21. The dimeric peptide of claim 20, wherein the IgG protein is IgG1.

22. A pharmaceutical composition comprising the polypeptide of claim 1 and a pharmaceutically acceptable carrier.

23. The polypeptide of claim 1, wherein the polypeptide is a fragment comprising at least domains D1 to D3.

24. The polypeptide of claim 1, wherein the polypeptide comprises the entire extracellular part of gp130.

* * * * *

UNITED STATES PATENT AND TRADEMARK OFFICE
CERTIFICATE OF CORRECTION

PATENT NO. : 8,501,696 B2  
APPLICATION NO. : 12/738807  
DATED : August 6, 2013  
INVENTOR(S) : Grotzinger et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 303 days.

Signed and Sealed this  
Third Day of December, 2013

Margaret A. Focarino  
*Commissioner for Patents of the United States Patent and Trademark Office*

UNITED STATES PATENT AND TRADEMARK OFFICE
CERTIFICATE OF CORRECTION

| | |
|---|---|
| PATENT NO. | : 8,501,696 B2 |
| APPLICATION NO. | : 12/738807 |
| DATED | : August 6, 2013 |
| INVENTOR(S) | : Joachim Grötzinger |

Page 1 of 1

It is certified that error appears in the above-identified patent and that said Letters Patent is hereby corrected as shown below:

In the Claims

Column 21, line 26 (claim 1, line 7) delete "Tip" and insert --Trp-- therefore.

Column 21, line 30 (claim 1, line 11) delete "Tip" and insert --Trp-- therefore.

Signed and Sealed this
Eleventh Day of March, 2014

Michelle K. Lee
*Deputy Director of the United States Patent and Trademark Office*